(12) United States Patent
McIntyre et al.

(10) Patent No.: US 7,794,458 B2
(45) Date of Patent: Sep. 14, 2010

(54) BIPOLAR RADIO FREQUENCY ABLATION DEVICE WITH RETRACTABLE INSULATOR

(75) Inventors: Jon T. McIntyre, Newton, MA (US); Isaac Ostrovsky, Wellesley, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1093 days.

(21) Appl. No.: 11/187,669

(22) Filed: Jul. 22, 2005

(65) Prior Publication Data

US 2007/0021745 A1 Jan. 25, 2007

(51) Int. Cl.
*A61B 18/14* (2006.01)

(52) U.S. Cl. .................................................. 606/41

(58) Field of Classification Search .............. 606/41, 606/1, 32, 42, 45, 48–50; 607/115, 116, 607/119, 122, 127
See application file for complete search history.

(56) References Cited

U.S. PATENT DOCUMENTS

| | | | | |
|---|---|---|---|---|
| 1,865,532 A * | 7/1932 | Lutz | .......................... | 219/63 |
| 2,626,368 A * | 1/1953 | Petersen | ................ | 313/231.21 |
| 3,442,105 A * | 5/1969 | Willis et al. | ................... | 72/56 |
| 4,311,143 A * | 1/1982 | Komiya | ......................... | 606/47 |
| 5,370,675 A * | 12/1994 | Edwards et al. | ............. | 607/101 |
| 5,507,743 A * | 4/1996 | Edwards et al. | ................ | 606/41 |
| 5,827,276 A * | 10/1998 | LeVeen et al. | ................. | 606/41 |
| 5,964,754 A * | 10/1999 | Osypka | ......................... | 606/37 |
| 6,108,582 A * | 8/2000 | Fischer, Sr. | .................. | 607/127 |
| 6,235,023 B1 | 5/2001 | Lee et al. | | |
| 6,402,746 B1 * | 6/2002 | Whayne et al. | ................ | 606/41 |
| 6,575,967 B1 * | 6/2003 | Leveen et al. | .................. | 606/41 |
| 6,641,580 B1 | 11/2003 | Edwards et al. | | |
| 6,652,516 B1 * | 11/2003 | Gough | ......................... | 606/41 |
| 6,911,019 B2 * | 6/2005 | Mulier et al. | ................ | 604/114 |
| 7,306,595 B2 * | 12/2007 | Ostrovsky et al. | .............. | 606/41 |
| 7,329,269 B2 * | 2/2008 | Shapiro et al. | .............. | 606/200 |
| 2002/0022864 A1 * | 2/2002 | Mahvi et al. | .................... | 607/2 |
| 2002/0133148 A1 | 9/2002 | Daniel et al. | | |
| 2002/0156472 A1 * | 10/2002 | Lee et al. | ........................ | 606/41 |
| 2004/0158239 A1 * | 8/2004 | Behl et al. | ..................... | 606/41 |
| 2004/0254572 A1 * | 12/2004 | McIntyre et al. | .............. | 606/41 |
| 2005/0101950 A1 | 5/2005 | Gough et al. | | |
| 2005/0234444 A1 * | 10/2005 | Hooven | ........................ | 606/41 |
| 2005/0251239 A1 * | 11/2005 | Wallace et al. | .............. | 607/126 |

FOREIGN PATENT DOCUMENTS

WO 2005/048861 6/2005

* cited by examiner

*Primary Examiner*—Lee S Cohen
(74) *Attorney, Agent, or Firm*—Vista IP Law Group LLP

(57) ABSTRACT

An ablation device, comprises a first tubular element and a first electrode which, when in an insertion configuration, is received within the first tubular element, the first electrode being deployable from the first tubular element to anchor in a target portion of tissue at a first electrode operative position in combination with a second electrode which, when in the insertion configuration, is received within the first tubular element, the second electrode being deployable from the first tubular element to anchor in the target portion of tissue at a second electrode operative position separated from the first electrode operative position, the second electrode being deployable independently of the first electrode and an insulating element movable relative to the first electrode to insulate selected portions of the first electrode. The device is employed to ablate first and second portions of tissue.

14 Claims, 3 Drawing Sheets

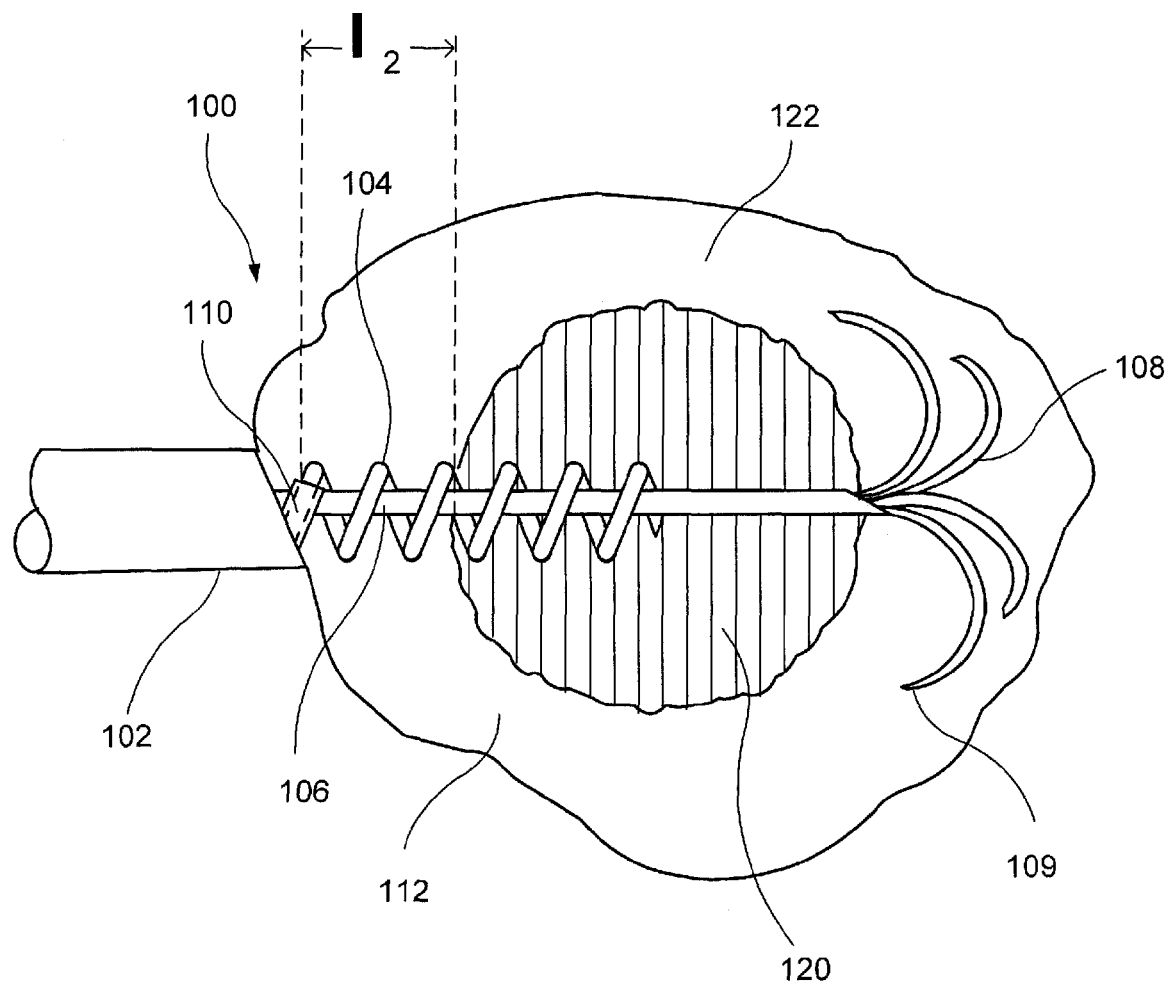
F I G. 2

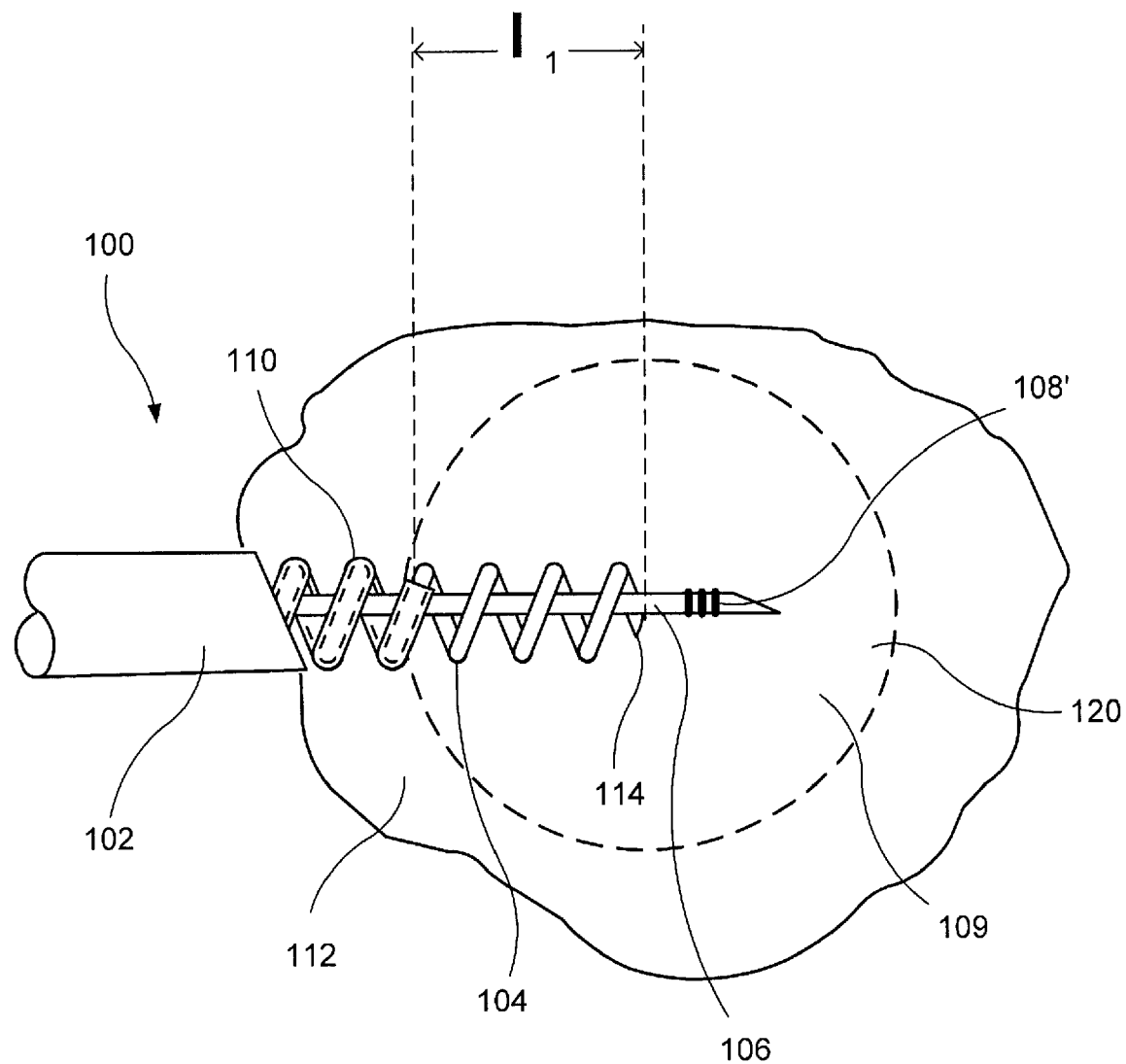
F I G. 3

BIPOLAR RADIO FREQUENCY ABLATION DEVICE WITH RETRACTABLE INSULATOR

BACKGROUND

Ablation is often recommended for the treatment for fibroids tumors and other tissue masses. Local ablation may be carried out by inserting a therapeutic device into target tissue and performing a therapeutic activity to destroy targeted cells. For example, electrical energy may be applied to the target tissue by discharging electric current from one or more electrodes placed in the target tissue. Alternatively, fluids with appropriate properties may be injected into the vicinity of the target tissue to chemically necrose the tissue.

Target tissues such as tumors and fibroids are often not securely anchored in place within the body, but instead are loosely joined to the surrounding tissue by ligaments and other structures. Accordingly, it may be difficult for a surgeon to insert a needle electrode or other energy delivery devices into the target tissue as the tissue may move as the surgeon attempts to puncture it with such a device. Grasping devices and anchors may be used to immobilize the tissue while an electrode is inserted thereinto, but this increases the complexity of the operation and may require additional incisions and/or assistance from additional personnel.

The size of the apparatus used to perform such procedures is minimized to reduce trauma to the patient. However, the small size of the ablation probe decreases the size of the ablation area. Because of the reduced size of the ablation region, it may be necessary to perform ablations of larger tissue masses in multiple stages at different locations before the entire volume of target tissue is ablated. In addition, the difficulty in inserting electrodes into many types of target tissues complicates the procedure and increases the time required for and the trauma associated with the procedure.

SUMMARY OF THE INVENTION

In one aspect, the present invention is directed to an ablation device, comprising a first tubular element and a first electrode which, when in an insertion configuration, is received within the first tubular element, the first electrode being deployable from the first tubular element to anchor in a target portion of tissue at a first electrode operative position in combination with a second electrode which, when in the insertion configuration, is received within the first tubular element, the second electrode being deployable from the first tubular element to anchor in the target portion of tissue at a second electrode operative position separated from the first electrode operative position, the second electrode being deployable independently of the first electrode and an insulating element movable relative to the first electrode to insulate selected portions of the first electrode.

The present invention is further directed to a method of ablating tissue, comprising anchoring a first electrode at a first location in a target portion of tissue, deploying a second electrode at a second location in the target portion of tissue and applying current between the first and second electrodes to ablate a first ablation portion of tissue between the first and second electrodes in combination with moving an insulative cover relative to the first electrode to move a conductive portion of the first electrode to a third location within the target tissue, the third location being further from the second location than the first location, moving the second electrode to a fourth location within the target tissue, the fourth location being further from the first location than the second location and applying current between the conductive portion of the first electrode and the second electrode to ablate a second ablation portion of tissue surrounding the first ablation portion of tissue.

BRIEF DESCRIPTION OF DRAWINGS

FIG. 2 is a schematic view showing the RF ablation device of FIG. 1 in a second configuration.

FIG. 3 shows another exemplary embodiment of the RF ablation device of FIG. 1.

DETAILED DESCRIPTION

Figure 1:
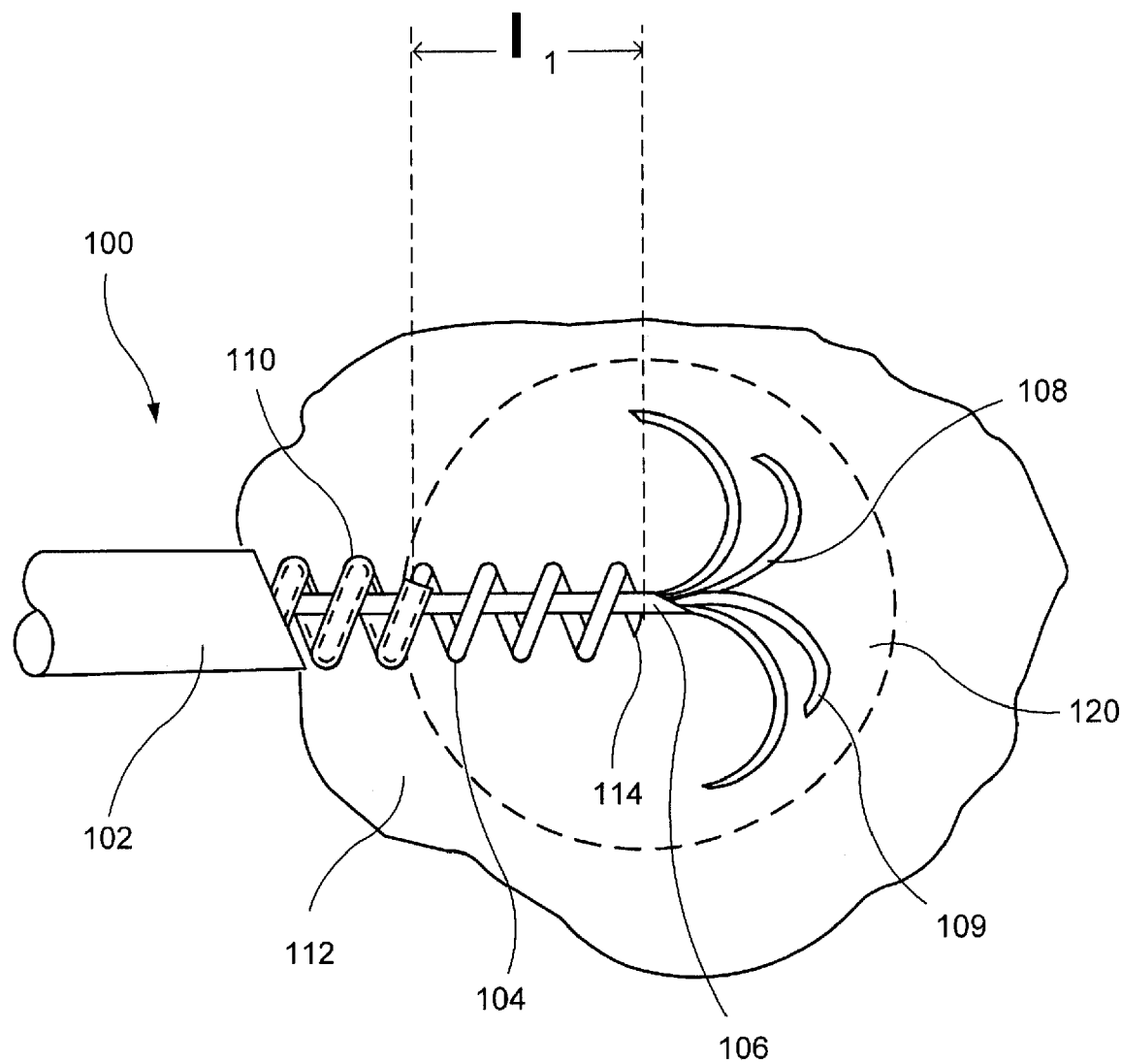
FIG. 1 is a schematic view showing the RF ablation device according to an embodiment of the invention in a first configuration.

The present invention may be further understood with reference to the following description and the appended drawings, wherein like elements are referred to with the same reference numerals. The present invention is related to medical devices used to destroy tissue less invasively. In particular, the present invention relates to devices for ablating tissue such as fibroids, tumors and other masses using electric energy provided through a needle-like device which is inserted into target tissue.

In one embodiment, the elements used to deliver therapeutic energy (such as electrical current) to the target tissue as well as the devices used to grasp and hold target tissue in place are both deployable from a single medical instrument. Thus, the number of incisions or punctures necessary to perform the medical procedure is minimized and the procedure can be carried out with a reduced number of personnel. Embodiments of the invention provide for a dual electrode device whose effective ablation volume may be changed while the device is inserted in the target tissue, without having to remove the device and re-insert it into the target tissue.

Conventional systems for ablating tissue with needle-based devices include, for example, the LeVeen Needle Electrode™ from the Oncology Division of Boston Scientific Corp. and the Starburst™ product line available from RITA Medical Systems, Inc. When using these devices, the surgeon punctures the target tumor with the device's needle and then deploys one or more radio frequency (RF) tines into the tissue mass. An electric voltage is then applied to the tines to ablate the target tissue.

It may be difficult to use these devices with many tumors or fibroids as these tissue masses may move as the surgeon attempts to insert the needle thereinto. As described above, the tissue masses are often only loosely held to the surrounding tissue by ligaments or connective tissues possibly requiring multiple attempts before the needle is positioned correctly. Alternatively, a grasping device such as a tumor screw may be used to immobilize and apply traction to the target tissue while the needle is inserted. This approach simplifies insertion of the needle into the tissue mass, but increases the complexity of the overall procedure, especially if multiple entry points through the skin are used to position the grasping device and the needle. Moreover, these procedures require the surgeon to manipulate several devices simultaneously, and may require the assistance of other personnel to complete the operation.

Many conventional RF tissue ablation devices are monopolar (i.e., electrodes of only one polarity are inserted into the target tissue with an exterior grounding pad drawing current from the electrodes, through the target tissue). Such monopolar RF ablation devices may cause damage to non-targeted tissue between the electrodes and the grounding pads including burns to the skin contacted by the grounding pad. In order to achieve desired ablation levels, monopolar delivery systems may require energy delivery times and power levels increased relative to those associated with bi-polar systems. However, monopolar RF ablation devices are used extensively because they operate with only a single electrode inserted per incision.

One embodiment of a tissue ablation system according to the present invention combines an array of radio frequency (RF) tines with an anchoring coil to form a device for the therapeutic treatment of target tissue masses including fibroids and tumors. In one exemplary embodiment, the anchoring coil used to stabilize the target tissue and to facilitate insertion of the needle also serves as one of the poles of a bipolar RF system with the tines forming the other pole of the bipolar system. This design offers the advantages of stabilization of the target tissue during insertion of the needle and deployment of the tines, as well as the increased efficiency and other benefits of delivering the RF energy through a bipolar electrode arrangement. Additional grounding pads are not required when using the system according to the invention, and the electrical energy delivery time is considerably shortened as compared to procedures using monopolar systems.

The tissue ablation system according to the invention also causes a larger lesion in the target tissue, by following a staged energy delivery approach in which the target tissue is ablated in two or more phases. As will be described in greater detail below, a first region is ablated while the two electrodes are in an initial position and a current flows therebetween. The location of the electrodes is then changed, without removing the device from the target tissue, and the application of current is repeated to ablate a second region of the target tissue. The process may be repeated additional times, depending on the specific configuration of the electrodes and on the size of the target tissue being treated.

In one exemplary embodiment, the location of a first electrode is varied within the target tissue by pushing the first electrode into the target tissue and by extending or withdrawing a movable insulating sleeve placed over the first electrode. For example, the insulating sleeve may be adapted to extend into the target tissue mass over an anchoring coil which serves as the first electrode. The insulating sleeve may be extended or retracted relative to the longitudinal length of the first electrode, to vary the size of a portion of the first electrode in effective contact with the target tissue mass.

In the context of this application, the portion of the first electrode in effective contact with the target tissue mass (area of effective contact) refers to an area surrounding a portion of the first electrode not covered by the insulating sleeve or by an insulating tubular element and which is in contact with target tissue that has yet to be ablated. In contrast, the portion of the first electrode within such an insulating sleeve or tubular element or which is in contact with target tissue which has already been ablated is not part of the area of effective contact as tissue which has already been ablated is not an effective conductor of electricity and behaves similarly to an insulating layer surrounding the electrode.

In an exemplary procedure for use of the device according to the invention, a distal region of the first electrode is extended from a distal end of an insulating sleeve or tubular element and inserted into a target tissue mass. The position of the insulating sleeve relative to the first electrode is then adjusted so that only a selected distal region of the first electrode is uncovered. The second electrode is also deployed in the target tissue mass so that a first portion 120 of the target tissue mass may be ablated in an initial ablation phase.

After completion of the initial ablation phase, the insulating sleeve may be withdrawn, to expose a more proximal region of the first electrode. As the initial ablation phase has ablated the tissue surrounding the distal end of the first electrode, this are is no longer part of the area of effective contact. The area of effective contact now includes the area surrounding the newly exposed, more proximal region of the first electrode. Also, the second electrode may be pushed further into the target tissue mass and re-deployed distally, outside of the portion of tissue ablated in the initial phase. The new locations of the effective contact areas of the first and second electrodes and the paths along which the current will pass between them define a second portion of the target tissue mass to be ablated with the second portion radially surrounding the first portion 120.

Once the first and second electrodes have been re-deployed to their new positions, a subsequent ablation phase is carried out. In the subsequent ablation phase, the second portion of the target tissue mass is ablated by applying a current between the effective contact areas of the first and second electrodes. As the conductivity of the ablated first portion 120 is greatly decreased, the current flows around the first portion 120 through a second portion of the target tissue mass surrounding the first portion 120, radially outward from it and forming a shell therearound.

FIG. 1 shows an exemplary embodiment of a bipolar RF ablation device 100 with a retractable insulating element according to an embodiment of the invention. FIG. 1 shows the configuration of the electrodes within a target tissue mass 112 during the initial ablation phase while FIG. 2 shows the configuration of the electrodes in a subsequent ablation phase. The device may include an insertion element such as first tubular element 102, which is used to guide the RF ablation device along a working lumen of an endoscope to a location adjacent to the target tissue 112. Alternatively, the first tubular element 102 may be a needle-like cannula used to pierce biological tissues, so that its distal end may be placed in proximity to the target tissue mass 112. Tubular element 102 can also be inserted into the patient via a trocar.

A first electrode 104 may extend from a lumen of the first tubular element 102, at the distal end thereof. The first electrode 104 is preferably shaped like a coil or a corkscrew and rotatably mounted within the tubular element 102 to allow it to be screwed into the target tissue mass 112. Alternatively, first electrode 104 can be fixed directly to the cannula 102, allowing them to be rotated together. A distal end 114 of the first electrode 104 is preferably formed as a sharpened tip to facilitate tissue penetration and the size and pitch of the coils of the first electrode 102 are selected to provide sufficient traction and gripping of the target tissue mass 112, without being so large as to cause unnecessary trauma to the patient during insertion. The first electrode 104 may also be biased to expand to a larger diameter after exiting the tubular element 102, to increase the grip on the target tissue mass 112 while maintaining a smaller profile during insertion and withdrawal of the device 100. The first electrode 104 is received within the tubular element 102 so that it may be rotated and translated longitudinally relative thereto. A proximal handle or similar operating device (not shown) may be provided to facilitate rotation and translation of the first electrode 104 relative to the tubular element 102.

An insulating sleeve 110 is received around the first electrode 104 and is slidable thereover to cover or uncover portions of the first electrode 104. The insulating sleeve 110 may preferably be formed as a tube following the coil-like shape of the first electrode 104. However, the insulating sleeve 110 may also be formed as a slidable shell surrounding encompassing an entire diameter of first electrode 104 without contacting an inner diameter thereof. As would be understood by those skilled in the art, various additional configurations of the insulating sleeve 110 may be employed so long as the sleeve and the electrode 104 are movable relative to one another to selectively expose and insulate portions of the first electrode 104. The insulating sleeve 110 may be formed of any suitable bio-compatible, electrically insulative material, such as polyimide, polyamide, polytetrafluoroethylene or other fluoropolymers.

The device 100 further includes, at a distal end thereof, a second electrode 108. An insertion element, shown in FIGS. 1 and 2 as a needle tubular element 106, may be used to contain a second electrode 108 prior to its deployment. The needle tubular element 106 is preferably substantially coaxial with the first electrode 104 and contained within the coils thereof. Thus, the first and second electrodes 104, 108 and the needle tubular element 106 are contained within a central lumen of the first tubular element 102 during insertion of the device 100 into the patient so that a profile of the device 100 is limited to an outer diameter of the tubular element 102. After the first electrode 104 has been anchored in the target tissue mass 112 as described above, the needle tubular element 106 is extended from the distal end of the tubular element 102 through the coil of the first electrode 104 into the target tissue mass 112. The second electrode 108 is then deployed from the needle tubular element 106 at a position separated from the distal end of the first electrode by a distance selected to control a size and shape of the first portion 120, as shown in FIG. 1. The second electrode 108 preferably comprises an array of tines 109, or a similar arrangement of multiple conductors. However, those skilled in the art will understand that, if desired, the second electrode 108 may be formed as a single conductive element. As shown in FIG. 3, second electrode 108' may also be formed as a needle or rod with one or more ring electrodes mounted to it. These ring electrodes may be activated independently of one another. Both the first tubular element 102, the needle tubular element 106 and the first and second electrodes 104, 108 may be formed, for example, of stainless steel, Nitinol, or other surgical metals as would be understood by those skilled in the art.

As described above, in the initial ablation phase depicted in FIG. 1, the first and second electrodes 104, 108 define a first portion 120 of the target tissue mass 112 which is to be ablated initially. For optimum performance, the effective contact areas of the first and second electrodes 104, 108, respectively, are substantially equal. In this case, the deployed length of the first electrode 104 and the position of the insulating sleeve 110 are selected so that an area of the first electrode 104 along the length $l_1$ is substantially equal to a longitudinal extent of the second electrode 108. An electric potential is applied to the first and second electrodes 104, 108, respectively, to pass a current through the first portion 120 of the target tissue mass 112 to necrose this tissue.

After completion of the initial ablation phase, the first and second electrodes 104, 108, respectively, are re-deployed as shown in FIG. 2 with the second tubular element 106 pushed further into the target tissue mass 112 so that its distal tip is outside the first portion 120. The insulating sleeve 110 is then withdrawn proximally into the first tubular element 102, to expose a more proximal portion of the first electrode 104 to the tissue therearound leaving the distal portion of the first electrode 104 anchored within the ablated tissue of the first portion 120. As described above, due to the change in the conductivity of the first portion 120, only that part of the first electrode 104 shown by the length $l_2$ is now in effective electrical contact with the surrounding tissue. Therefore the insulating sleeve 110 is preferably position so that the effective tissue contact area of the first electrode 104 is substantially equal to the effective tissue contact area of the tines 109 of the second electrode 108.

After the first and second electrodes 104, 108 and the insulating sleeve 110 have been positioned as desired as shown in FIG. 2, a voltage is applied therebetween to cause current to flow around the non-conducting ablated tissue of the first portion 120 to ablate the second portion 122. This procedure may then be repeated to ablate additional surrounding portions of tissue until the entire volume of the target tissue mass 112 has been ablated. This multi-step procedure allows larger volumes of tissue to be ablated without removing and reinserting the ablation device 100.

An exemplary procedure to ablate a uterine fibroid is now described. During this procedure, the first tubular element 102 is inserted into the abdomen of a patient percutaneously or through a trocar until the distal end of the first tubular element 102 is positioned against the fibroid. The coil of the first electrode 104 is then extended from the distal end of the tubular element 102 to insert the tissue penetrating distal tip 114 thereof into the target tissue mass 112. The first electrode 104 is then rotated to screw the first electrode 104 into the mass of the fibroid (i.e., the target tissue mass 112) to anchor the first electrode 104 therein. The needle tubular element 106 is then inserted into the target tissue mass 112, until its distal tip extends at or beyond the first electrode 104. Once in position, the array of tines 109 is deployed from the tip of the needle tubular element 106 and electrical energy is applied between the first and second electrodes 104, 108 to ablate the first portion 120.

In the second step, the array of tines 109 is withdrawn into the second tubular element 106, which is then pushed a further distance into the fibroid tissue 112, further away from the first electrode 104. The array 109 is then re-deployed outside of the first ablation portion 120. The insulating sleeve 110 is withdrawn into the first tubular element 102 to expose a non-insulated length of the first electrode 104 which is outside of the first ablation portion 120. The current is then re-applied between the two electrodes, to form a second ablation portion 122.

The present invention has been described with reference to specific exemplary embodiments. Those skilled in the art will understand that changes may be made in details, particularly in matters of shape, size, material and arrangement of parts. For example, although the invention was described in the context of the treatment of uterine fibroids, other tumors may also be treated. Accordingly, various modifications and changes may be made to the embodiments. Additional or fewer components may be used, depending on the condition that is being treated using the described anchoring and RF ablation devices. The specifications and drawings are, therefore, to be regarded in an illustrative rather than a restrictive sense.

What is claimed is:

1. An ablation device, comprising:
    a first tubular element;
    a first electrode which, when in an insertion configuration, is received within the first tubular element, the first electrode being deployable from the first tubular element to anchor in a target portion of tissue at a first electrode operative position;
    wherein the first electrode is formed as a self-anchoring coil with a tissue penetrating tip;
    a second tubular element movable relative to the first tubular element to extend from the first tubular element and penetrate a target portion of tissue;

a second electrode which, when in the insertion configuration, is received within the second tubular element, the second electrode being deployable from the second tubular element to anchor in the target portion of tissue at a second electrode operative position separated from the first electrode operative position, the second electrode being deployable independently of the first electrode; and an insulating sleeve received around the first electrode comprising a shell encompassing an entire diameter of the first electrode without contacting an inner diameter of the first electrode, the insulating sleeve being movable relative to the first electrode to insulate selected portions of the first electrode.

2. The ablation device according to claim 1, wherein the second electrode comprises an array of tines.

3. The ablation device according to claim 2, wherein the array of tines is substantially umbrella-shaped.

4. The ablation device according to claim 1, wherein the coil of the first electrode has a diameter which increases after deployment from the first tubular element.

5. The ablation device according to claim 1, wherein the second tubular element is substantially coaxial with the first electrode.

6. The ablation device according to claim 1, wherein the first tubular element includes a tissue penetrating distal tip.

7. The ablation device according to claim 6, wherein the first tubular element defines a lumen which, in the insertion configuration, contains the first and second electrodes.

8. The RF tissue ablation device according to claim 1, wherein the insulating element is formed of one of polyimide, polyamide, polytetrafluoroethylene and a fluoropolymer.

9. An ablation device according to claim 1, wherein the second electrode is a needle electrode.

10. An ablation device according to claim 1, wherein the second electrode comprises multiple ring electrodes that can be independently electrically activated.

11. An ablation electrode assembly, comprising:

an insertion tubular element;

a first electrode comprising a coil which, in an insertion configuration, is received within the insertion tubular element, the first electrode being deployable from the insertion tubular element to anchor at a first location in a target portion of tissue;

wherein the first electrode is formed as a self-anchoring coil with a tissue penetrating tip;

an insulating sleeve received around the coil comprising a shell encompassing an entire diameter of the coil without contacting an inner diameter of the coil, the insulating sleeve being movable relative to the first electrode to insulate selected portions of the first electrode;

a needle tubular element movable relative to the insertion tubular element to extend from the insertion tubular element and penetrate a target portion of tissue; and a second electrode which, when in the insertion configuration, is received within the needle tubular element, the second electrode being deployable from the needle tubular element to anchor at a second location within the target portion of tissue.

12. The electrode assembly according to claim 11, wherein the second electrode comprises an array of tines.

13. The electrode assembly according to claim 11, wherein the insulation element is movable along the first electrode to vary a length of a non-insulated portion thereof.

14. The electrode assembly according to claim 11, wherein the second electrode is movable along a longitudinal axis of the first electrode.

* * * * *